United States Patent [19]

Webb

[11] Patent Number: 5,381,649
[45] Date of Patent: Jan. 17, 1995

[54] MEDICAL STAPLE FORMING DIE AND PUNCH

[76] Inventor: Stephen A. Webb, Bioski Rd., Middlebury, Conn. 06762

[21] Appl. No.: 71,100

[22] Filed: Jun. 4, 1993

[51] Int. Cl.⁶ .................... B21D 53/46; B21G 7/02
[52] U.S. Cl. .............................. 59/75; 59/71; 59/77
[58] Field of Search .............. 59/71, 72, 73, 75, 77

[56]  References Cited
U.S. PATENT DOCUMENTS

| | | | |
|---|---|---|---|
| 1,727,574 | 9/1929 | Tibbals | 59/77 |
| 2,033,613 | 3/1936 | Crosby | 59/77 |
| 2,128,443 | 8/1938 | Vogel | 59/77 |
| 2,431,812 | 12/1947 | Lang | 59/77 |
| 2,857,735 | 10/1958 | Mashl | 59/77 |
| 5,060,468 | 10/1991 | Matsutani et al. | 59/74 |
| 5,303,539 | 4/1994 | Neamtu | 59/72 |

*Primary Examiner*—David Jones
*Attorney, Agent, or Firm*—Lawrence Hager

[57]  ABSTRACT

A medical staple forming die and pusher punch for use in a staple forming machine. The bend radius of the staple is formed either by the form punch pushing the wire past a set of rollers, or by movable forming dies in conjunction with a tapered or contoured pusher punch. Since the wire is not scrapping on a stationary rail, pulling thin or cracking in its corners is substantially eliminated and the possibility of metal slivers produced by the prior art scrapping methods is substantially reduced or eliminated.

13 Claims, 11 Drawing Sheets

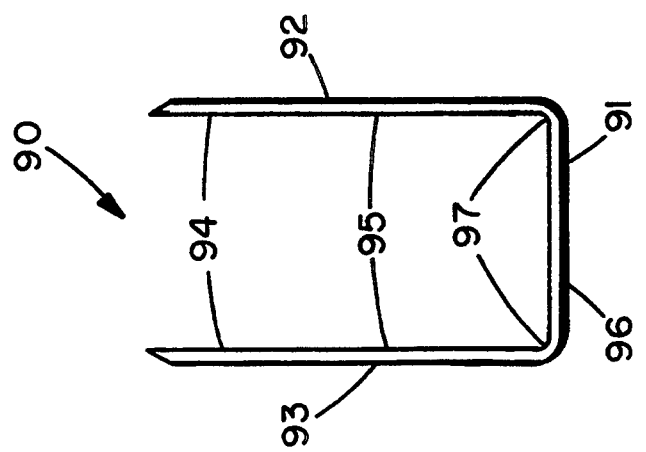
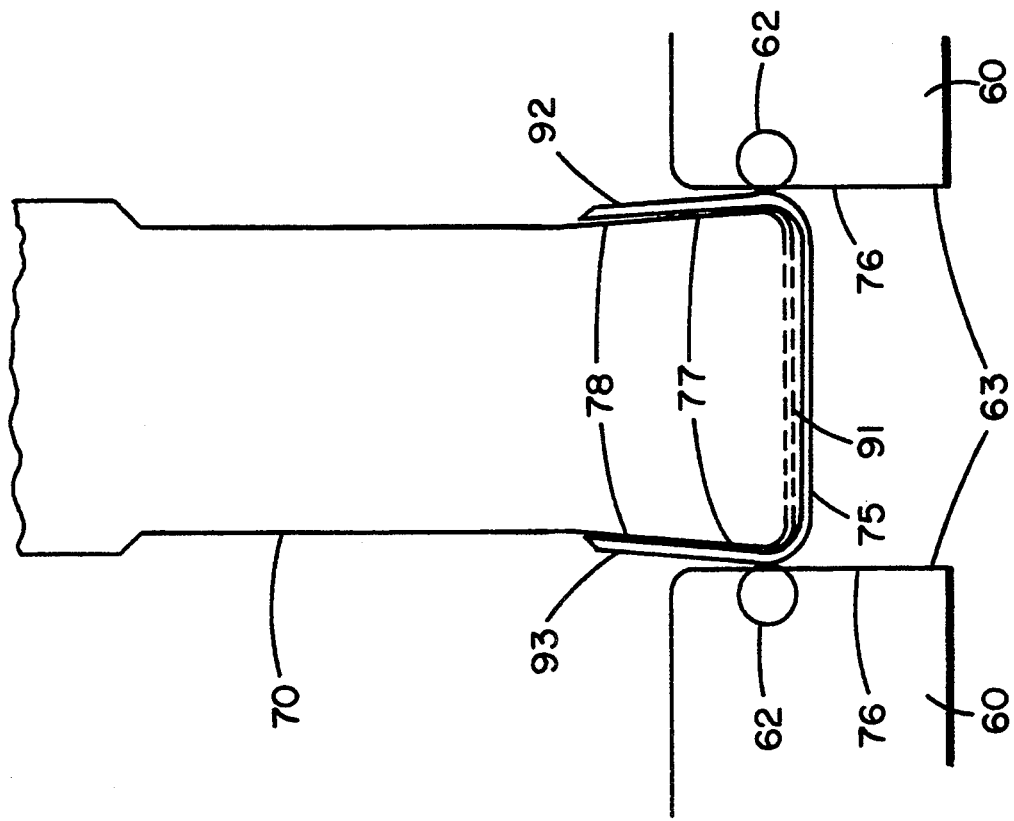

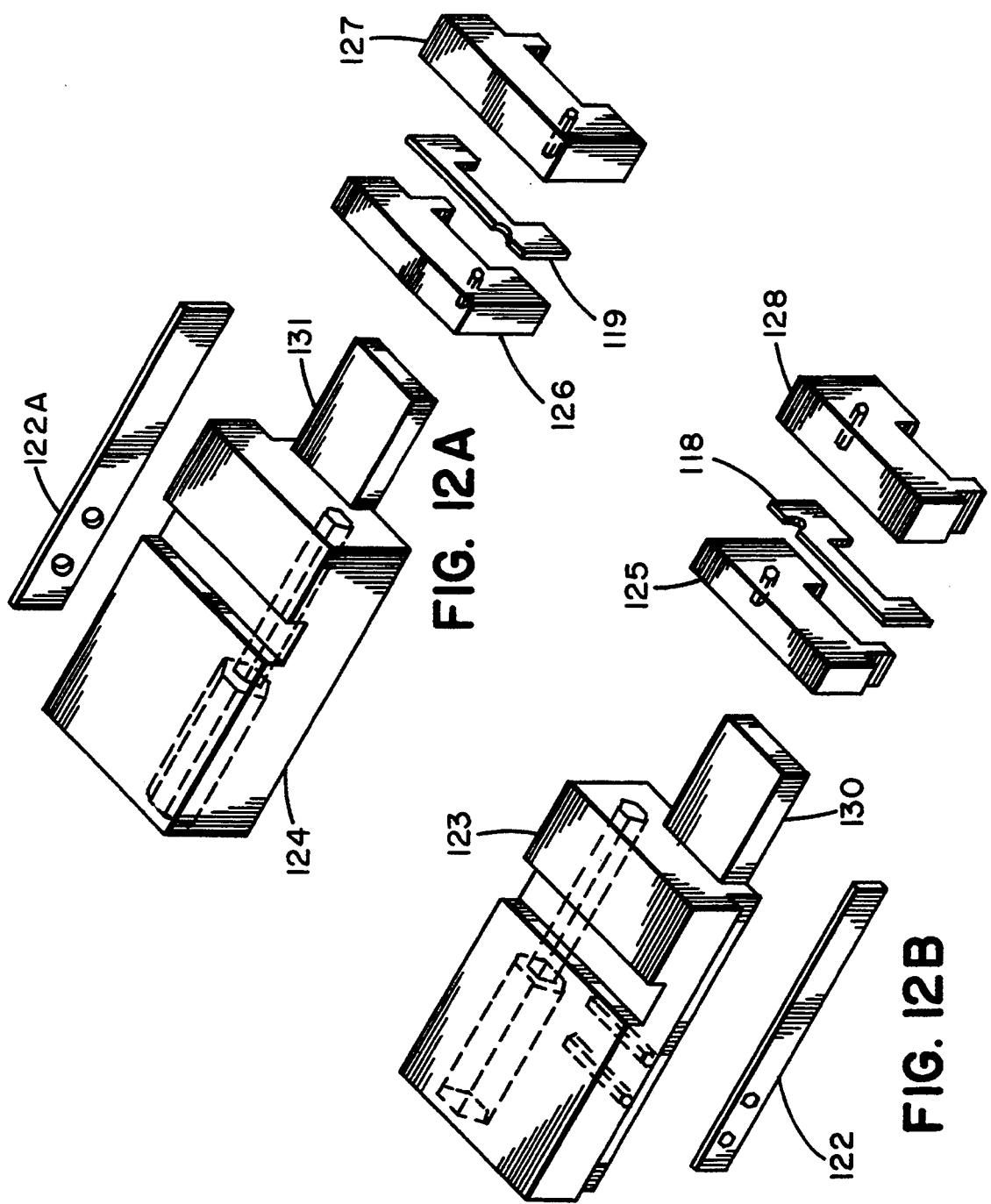

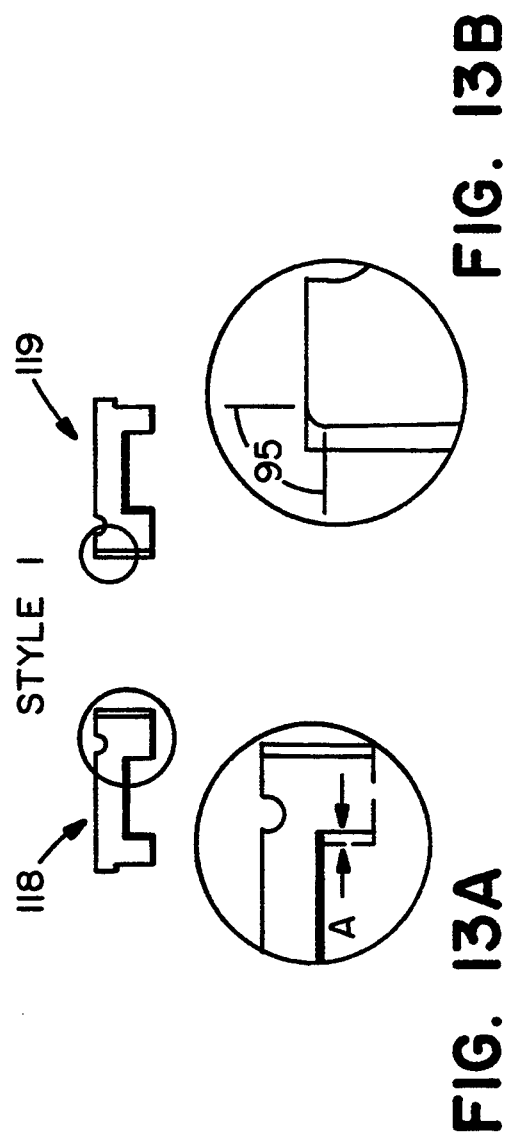
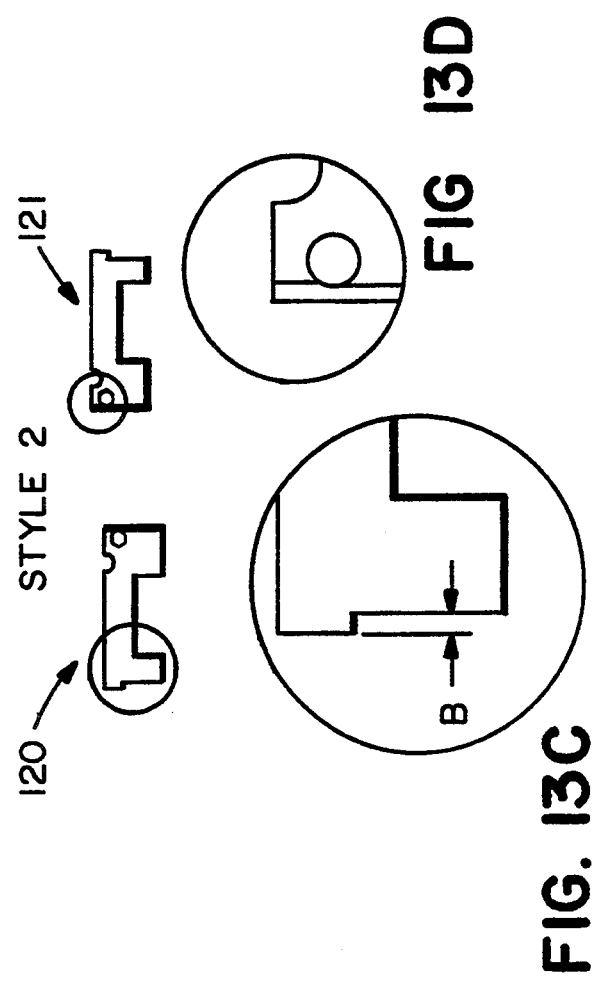

MEDICAL STAPLE FORMING DIE AND PUNCH

FIELD OF THE INVENTION

This invention relates to staple forming machines and, in particular, to a new die/punch for forming surgical type staples and method for forming same.

BACKGROUND OF THE INVENTION

Typically, the prior art method of forming a staple was to cut the wire by a cutoff punch to the desired length, and pushing the wire through a set of fixed dies. The wire was caused to bend and scrape between the non-movable rigid ridged surfaces of the die and a relatively straight walled pusher punch. This causes slivers or flakes of wire material to scrape loose and be deposited unto the legs of the staple. In addition, this rigid scraping caused the corner radius (bends) to weaken and/or crack the wire staple.

It should be obvious that metal filings on and cracks or weakened staple legs are of particular concern and hazardous in the medical art field, where these staples are utilized on/in the human body.

BRIEF STATEMENT OF THE PRIOR ART

The prior art includes several types of machines for forming shackles and staples which empty a die and pusher punch.

One such prior art machine is illustrated in U.S. Pat. No. 1,938,915 issued Dec. 12, 1933 to J. W. Leighton. This patent describes a machine for forming U-shaped shackles or bolts. A heated rod is confined between a pair of recessed blocks and a pair of pivotal die blocks to partially deform/bend the heated rod. Next, a center ram affects the upward bending of the bar to form the U-shaped shackle.

It is noted that this two step bending procedure is used to form bolt shackles and not medical staples. The rod or straight bolt is prevented from elongation by being compressed between a pair of blocks. The rod is heated to facilitate bending. The ram does not appear to have inwardly tapered intermediate side walls. The rod or bolt does not appear to be bent beyond parallel by this machine and is so limited by the parallel grooves or sides of the inner ram.

Another prior art patent of interest is U.S. Pat. No. 104,184 issued Jun. 14, 1970 to P. Miles. This patent describes a machine for forming a metal tack used on wood products. This patent reference does not relate to the manufacture of medical staples. This patent reference does not appear to be concerned with metal filing contamination on the tack.

Other prior art patents of interest include U.S. Pat. Nos. 173,909 issued Feb. 22, 1876 to S. S. Coutz & W. E. Rennard; 246,340 issued Aug. 30, 1881 to J. Rauschenberger & B. Dean; 354,166 issued Dec. 14, 1886 to W. F. Moody; 505,862 issued Oct. 3, 1893 to A. S. Thompson; 659,111 issued Oct. 2, 1900 to G. E. Soper; 707,006 issued Aug. 12, 1902 to G. F. Pross & A. P. Tucker.

These prior art patents are mentioned as being representative of the prior art and other pertinent patents/references may exist. None of the above cited patents are deemed to affect the patentability of the present claimed invention.

In contrast to the prior art, the present invention provides a die and punch for use in a staple forming machine to form medical staples, which (medical) staples have requirements and needs not recognized and not solved by the prior art. For example, the medical staple should be substantially, if not totally, clean, i.e., devoid of metal slivers or particle filings, and virtually without cracks or weakened corner radius portions caused by the bending operation. Also, the medical staple and method of manufacture must be low cost to constrain medical costs to the public. The present invention provides a solution to the aforementioned medical (staple) needs by providing a forming die designed to virtually eliminate any scraping, pulling or cracking of the wire used to form the medical staple.

The present invention, in contrast to the prior art, provides a staple forming die having glide or roller means to substantially eliminate scraping of the wire against the die rails; and a forming punch having a bottom guide groove with a curved corner radius to substantially eliminate bend angle cracking and provide for desired curved or contoured wire bend angle, and a contoured body portion having a relief angle to facilitate over bending of the wire to produce a staple with a corner radius that has substantially improved wire diameter uniformity over a desired bend radius to provide a medical type staple having relatively improved parallel staple legs normal to the base member which is substantially cleaner and stronger.

SUMMARY OF THE INVENTION

A staple forming punch, comprising:
 a body member having intermediate sloped or contoured portions defining a staple leg relief angle; and
 a head member having a wire guide groove with side curved corners having a desired radius to facilitate staple wire bending over while substantially eliminating or preventing staple wire cracking or thinning while undergoing formative bending over said curved corners of said head member.

A staple forming die, comprising:
 a pair of spaced apart rail members each having wall portions defining a glide/roller/bearing receiving alcove;
 a glide or roller or bearing member mounted within each alcove.

A new and improved die and punch having particular utility for forming a medical type staple, in combination comprising:
 a punch having a body member with sloped portions defining a relief angle, and a head member having a wire guide means and curved edges with predetermined radius of curvature; and
 a die having a pair of spaced apart rail members to accommodate insertion of said punch therebetween, and having roller means mounted to each rail member for engagement with the staple wire for effecting non-scraping bending of the staple wire with said punch urging the staple wire between the aligned roller means.

A method of forming a medical staple, comprising the steps of:
 cutting a strip of wire to a desired length;
 engaging said strip of wire by a pusher punch having guide rails;
 disposing said pusher punch and, thereby, said strip of wire between a pair of aligned roller or glide or bearing means mounted on opposing die rails;
 bending said staple wire between said roller or glide or bearing means at two intermediate portions over respective curved portions of said pusher punch to effect staple bends having a desired radius of curvature;

whereby a medical staple is produced having relatively few or virtually no bend angle cracks, with substantially parallel legs being substantially normal to the center or base portion of the staple, and being relatively free of metal slivers.

OBJECTIVES OF THE INVENTION

It is an object of the invention to provide a new and improved die for use in producing medical type staples.

It is a further object of the invention to provide a die having a pair of spaced apart aligned rollers mounted to the die rails.

It is a further object of the invention to provide a die having means for eliminating scraping of the work piece or staple wire against the rails of the die.

It is a further object of the invention to provide a new and improved pusher punch for producing medical staples.

It is a further object of the invention to provide a pusher punch having bottom guide rails or a groove dimensioned for receiving and guiding a strip of wire to form a medical staple.

It is a further object of the invention to provide a pusher punch having curved corners to guide and form the staple bend angle of curvature.

It is a further object of the invention to provide a pusher punch having intermediate sloped wall portions to enable over bending and bounce back of the staple legs during the bending process.

It is a further object of the invention to provide a method and apparatus for producing medical staples having improved strength and uniformity and substantially free of metal slivers.

It is a further object of the invention to provide a method and apparatus for producing medical staples having bends conforming to predetermined radius of curvature.

It is a further object of the invention to produce medical staples having relatively few or no metal cracks from bending of the metal wire to form the staple.

It is a further object of the invention to produce medical staples having relatively improved parallel legs each being relatively normal to the intermediate beam.

It is a further object of the invention to provide a method and apparatus for producing medical staples having substantially fewer defects.

It is a further object of the invention to provide a method and apparatus for producing medical staples relatively less expensively.

Other objects and advantages will be apparent to those skilled in the art from the detailed description of the drawings.

BRIEF DESCRIPTION OF THE DRAWINGS

The accompanying drawings illustrate the preferred embodiments of the present invention by way of example. Like numerals refer to like parts throughout.

FIG. 6 is an illustrative view of a medical staple being formed in accordance with the invention;

FIG. 7 is an illustrative view of a medical staple produced in accordance with the present invention;

FIG. 12 is an exploded view of a spring loaded forming die alternative embodiment of the present invention;

FIG. 13 illustrates in greater detail features of the forming die shown in FIG. 12;

DETAILED DESCRIPTION OF THE INVENTION

Figure 1:
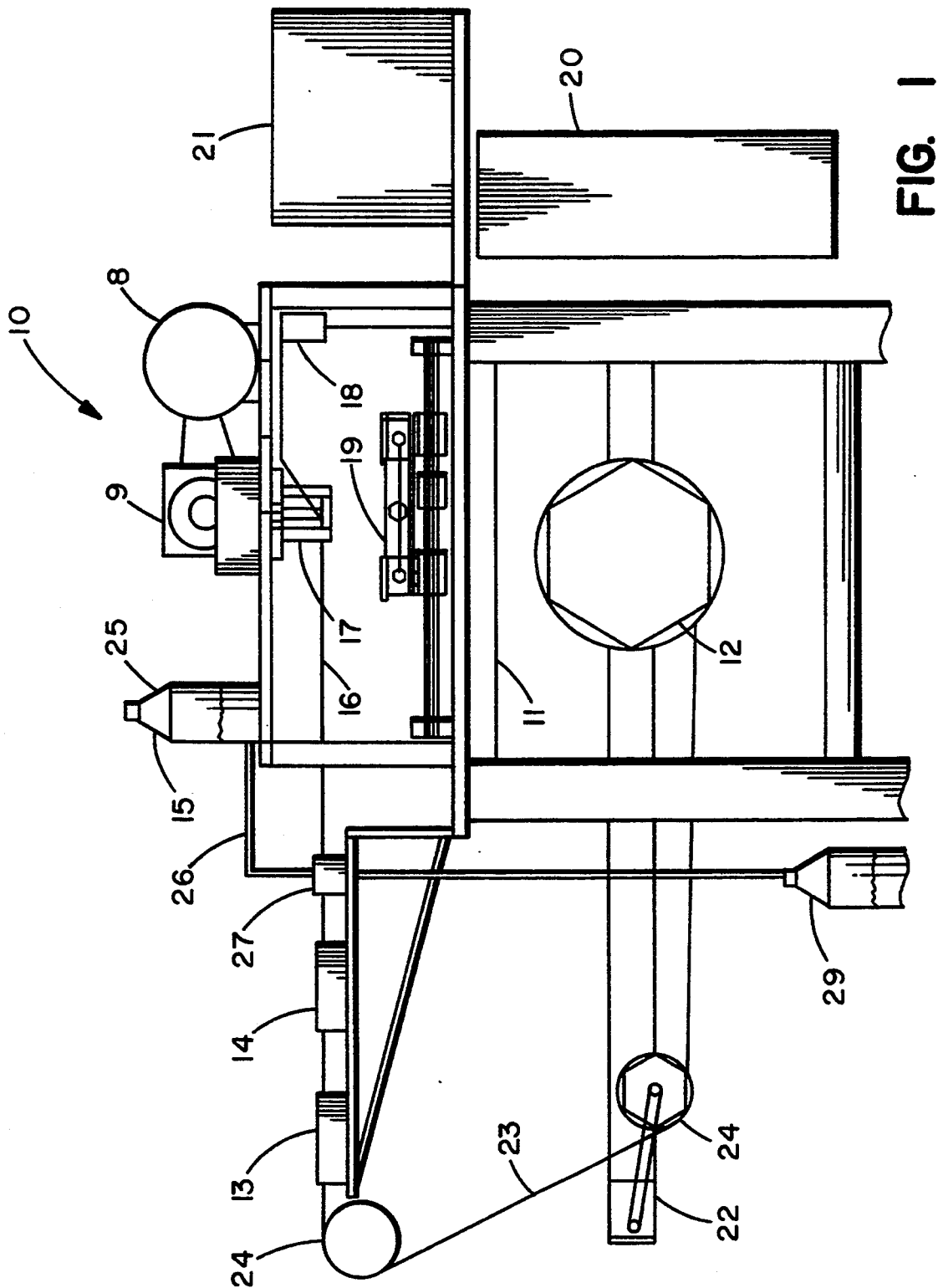
FIG. 1 is a plan view of a staple forming machine.

Referring to the drawings, particularly FIG. 1 there is illustrated a typical prior art staple forming machine. Since the basic function of such prior art machines are well known, a detailed description of operation will not be provided herein to avoid prolixity.

Briefly stated, the typical staple forming machine or apparatus 10 comprises a base table 11, a wire spool feed mechanism 12, a wire straightener 13, an air press feed device 14, a wire wash/lubrication means 15, a wire feed tube 16, a staple forming head device or mechanism 17, an air-vac vacuum pump 18, an X-Y positioning table 19, an electronic power panel 20 and a controller 21.

The wire spool feed mechanism 12 is driven by a conventional electrical motor, for example, a RPM motor. The motor on/off signal to the dive motor (not shown) is provided by a micro-switch (not shown) on the slack take-up assembly 22.

The wire 23 is passed over a guide roller 24 and is straightened by pulling it through a wire straightener 13, such as a Sjogren model 715A.

The wire 23 is fed by a rapid-air press feed 14 that has been modified to feed wire. Since this is conventional and does not form part of the invention a detailed discussion thereof will be avoided.

Following the press feed 14 station, the wire is pushed through the lubrication station. The lubrication station generally comprises a wire wash/lubrication device 15 having a source of liquid lubrication 25 connected via conduit 26 to a wash/lubrication chamber 27. The process and technique of wire lubrication may be of conventional design. The wire 23 is pushed through chamber 27 and bathed with the lubricating fluid.

Next, the wire 23 is pushed into the wire forming head 17. The design of the wire forming head (with the exception of the die and punch described hereinafter in detail) may be of conventional design. An air-vac vacuum system is provided which generally includes a vacuum pump 18 connected, via tubing 16, to the wire forming head 17 and to a collection container 29. Generally speaking, the vacuum system is provided to vacuum clean the wire forming head 17. The vacuumed oil/lubrication fluid on the wire and other debris are collected within container 29.

The operation of the staple forming machine and wire positioning are under the control of a machine controller or micro-processor 21, an X-Y positioning table 19 and a power source 20, each of conventional design. Typically, the length of the wire is monitored via sensors within the staple forming head 17. The positioning of the wire is generally controlled by table 19. The length of wire feed is controled by feeder 14 and monitored by sensors in the head 17.

Figure 2:
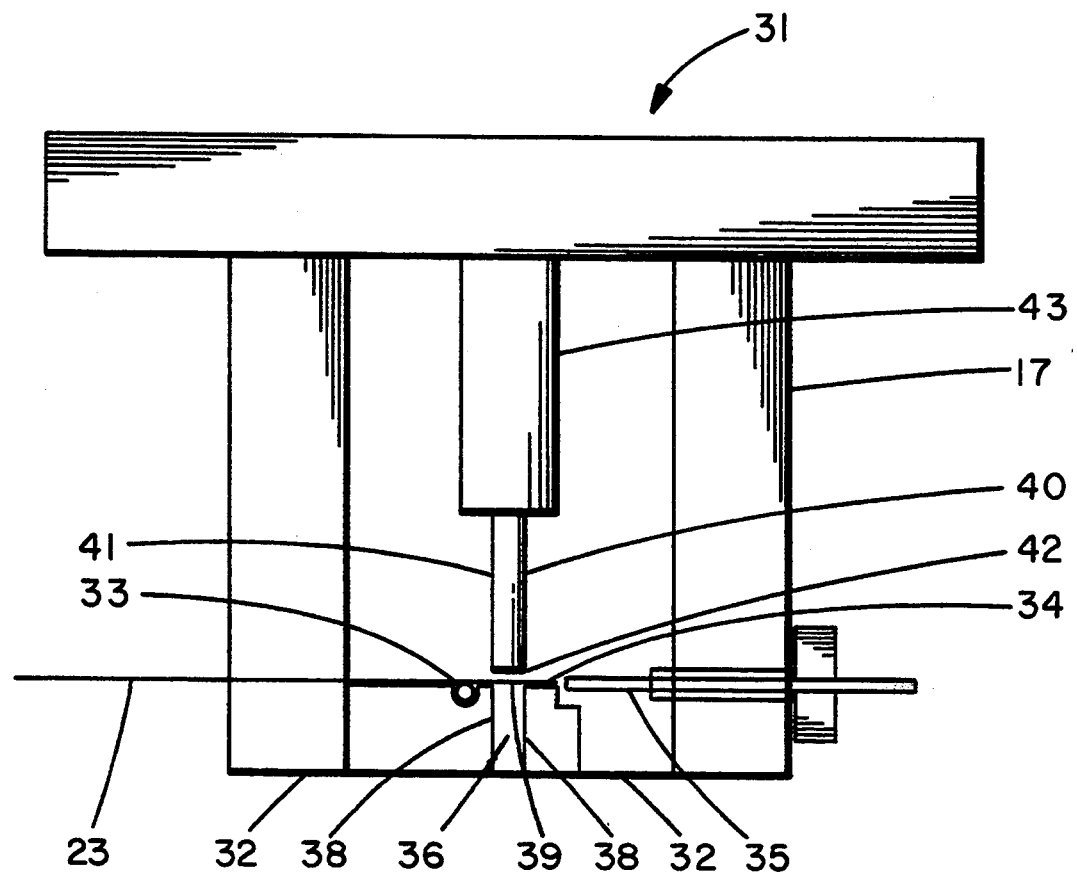
FIG. 2 is a plan view of a typical prior art die and punch arrangement utilized to form prior art medical staples.
Figure 3:
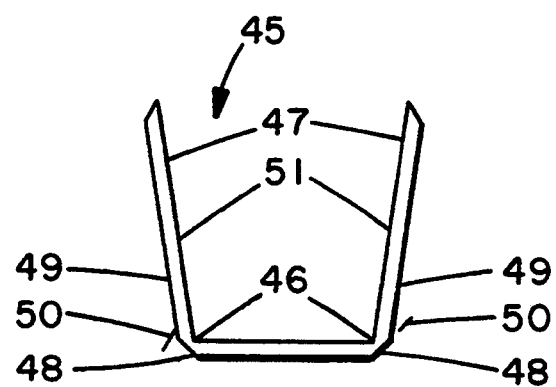
FIG. 3 is an illustrative view of a prior art staple formed in conventional manner.
Figure 4B:
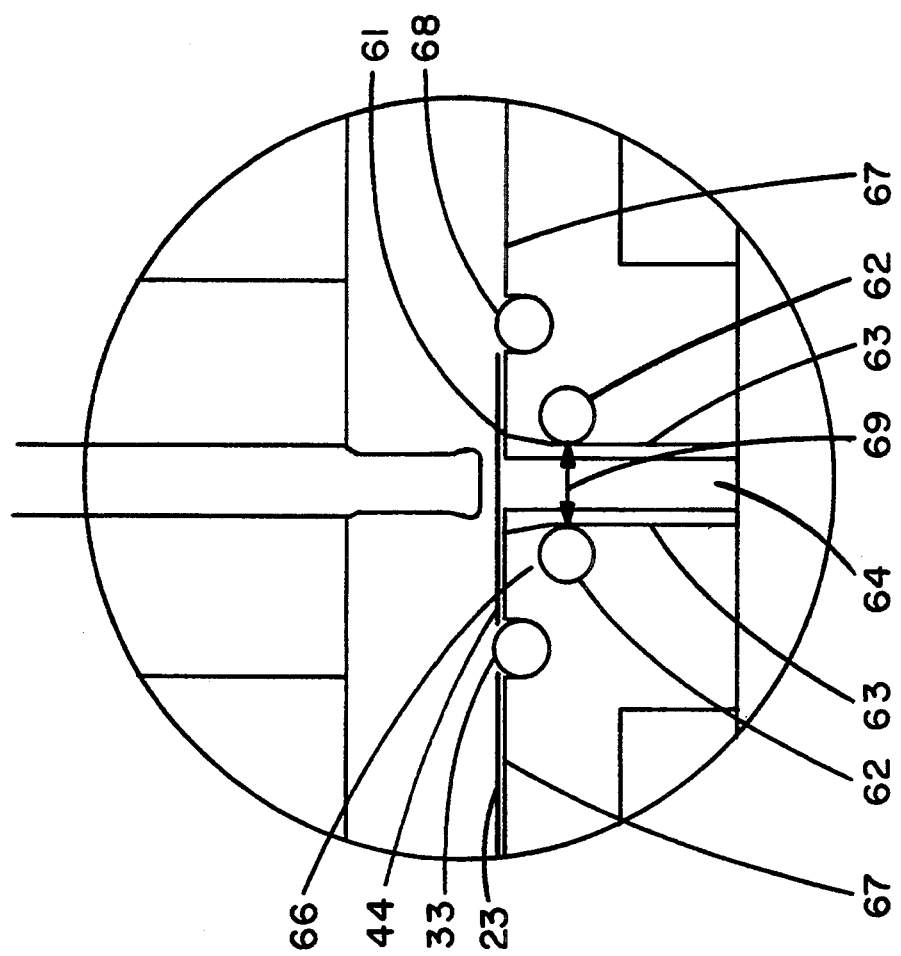
FIG. 4B is an enlarged view of a portion of the die and punch illustrated in FIG. 4.
Figure 4A:
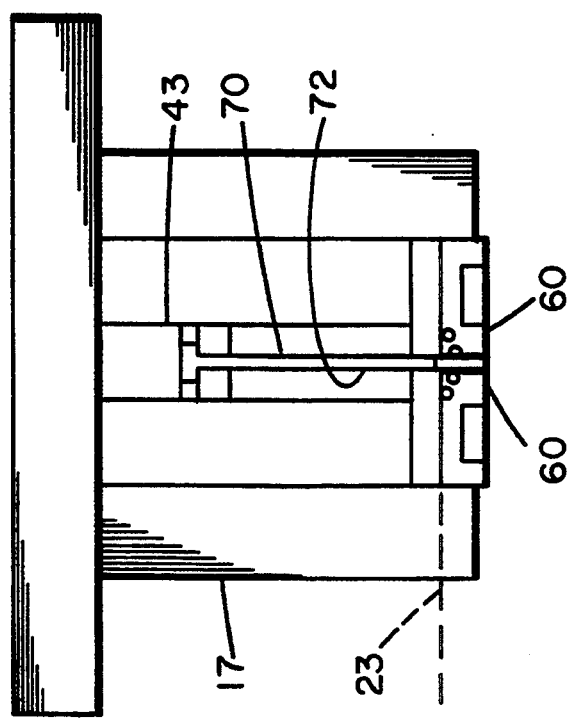
FIG. 4A is a partially cut away plan view of a die and punch in accordance with the present invention.
Figure 5:
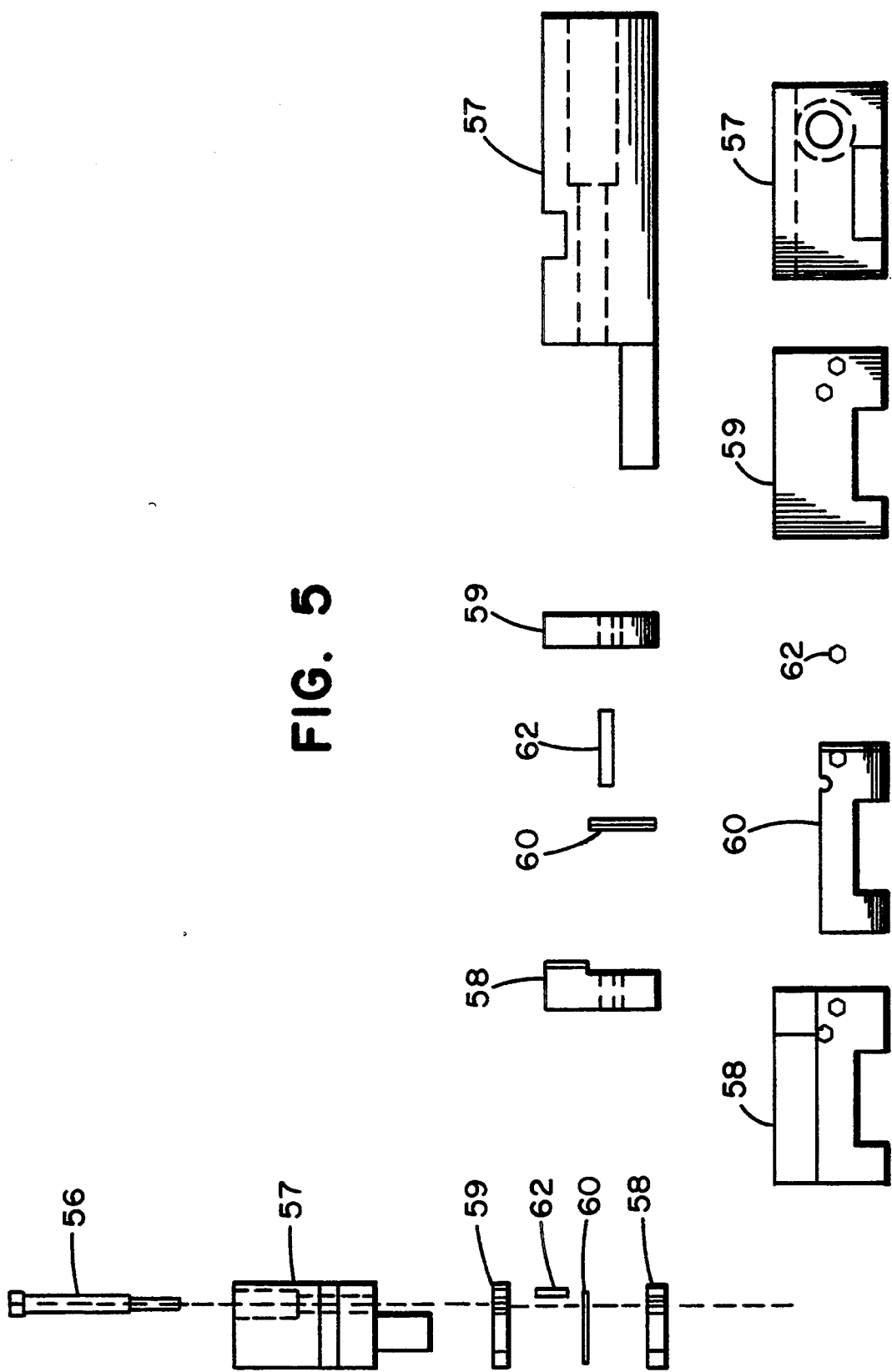
FIG. 5 is an exploded plan view of the forming die shown in FIG. 4.
Figure 8B:
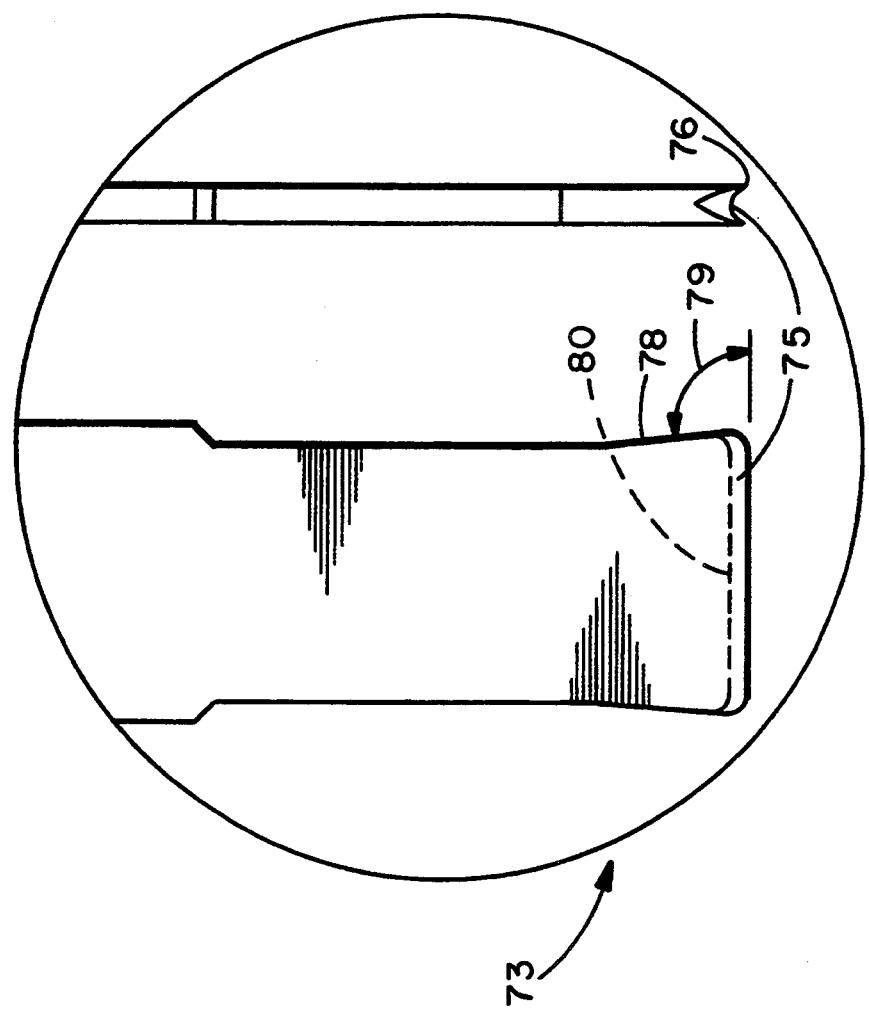
FIG. 8 is a more detailed illustrative view of the pusher punch in accordance with the invention.
Figure 8A:
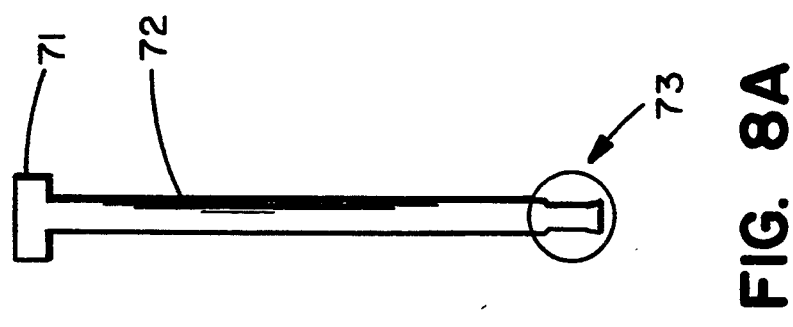

With reference now to FIGS. 2 and 3, the prior art staple forming die and punch, along with a typically formed staple will be discussed.

The die assembly 31 generally includes a pair of spaced apart forming spacers or rails 32 and a cutting punch 33. The wire 23 is pushed into the staple forming head 17 until its end tip 34 abuts against a probe sensor 35. The probe sensor 35 is located to detect when the wire 23 is feed to the desired length. Probe sensor 35 is coupled to the controller unit 21, which activates, via signal leads not shown, the clutch to cause a cam driven shaft activation of cutting punch 33.

Die assembly 31 has spacers 32 which are spaced apart to form die cavity 36 into which the prior art pusher punch 41 is driven. The side walls 38 of the die spacers 32 are substantially straight and spaced apart a distance for snugly squeezing the cut wire strip 39 on both sides of the straight side walls 40 of prior art pusher punch 41 and the spacer side walls 38, with said pusher punch 41 being driven downwardly into die cavity 36.

Pusher punch 41 has virtually ninety degree edge corners 42 and straight parallel side walls 40.

Accordingly, the prior art technique for producing medical staples resulted in seriously defective staples 45. Staple 45 is formed by bending at point 46 wire strip about the virtually square edge corners 42 of pusher punch 41. The staple legs 47 are roughly drawn and force fitted between the opposing walls 40 of pusher punch 41 and spacer die walls 38 causing a scraping of legs 47 with die wall 38. This bending and scraping action typically results in cracks 48 about the staple bends 46 and an elongation of the wire legs 47. As the legs 47 are drawn between the die spacers 32 and the pusher punch 41, the diameter or thickness 49 of the two legs 47 are reduced or narrowed at corners 46. The narrowing of the leg diameters 49 results in a diminished staple leg strength and narrowing of the bend radius, cracking and slivers. The drawing and scraping action generally also causes small metal slivers 50 to be produced which cling to the staple legs 47. Also the wire becomes contaminated with metal from the tooling, which may cause rusting and infections.

In addition, typically the staple legs 47 when released from confinement between the die 32 and punch 41, bows outwardly 51 such that the two legs 47 are not parallel as depicted in FIG. 3.

It should be recognized that such metal slivers 50, narrowing of leg diameters 49 and leg bowing (non-parallelism) 51 are of particular concern in the medical staple art field. For example, the metal slivers 50 can contaminate the sutured sound, and the cracked 48 and narrowed sections 49 of staple legs 47 can result in staple failure or braking after a wound has been stapled. In addition, the non-parallel legs 47 can result in failure to properly staple a wound or that the staple does not properly maintain the wound closed.

The above noted problems and defects have been long recognized but unresolved in the prior art medical staple field.

With reference now to FIGS. 4-8, the forming dies 60 and form punch 70 configured and arranged in accordance with the present invention will now be described.

Each forming die section 60 contains a somewhat bevelled upper edge corner 61, a pair of roller means 62 and wall portions 63 defining die cavity 64.

A pair of roller means 62 are rotatably mounted each to a respective forming die section 60 by conventional means. For example, the rollers 62 turn in holes ground into the stripper and cut-off die which acts as bushings. The rollers are captivated by punch block 58 and foot block 59. such as, for example, bolt 65. Alternatively, roller means 62 may be mounted to an outwardly biased hinge means, not shown, for providing positive inward pressure of the wire 23 being formed into a staple. Each roller means 62 is ideally mounted such that the top 66 of each roller is substantially even, i.e., lies in the same horizontal plane, with the top surface 67 of each forming die section 60. However, for practical reasons such as roller and die sizes, the present preferred embodiment, which appears to function well, utilizes a curved bevelled top surface edge 61 with the roller means 62 being mounted slightly below bevelled top surface edges 61. The specific mounting disposition of roller means 62 to the respective die sections 60 may be empirically determined for best results with consideration to the type of wire (metal alloy) and staple leg length being used. Each roller 62 projects outwardly from the respective die section 60 into die cavity 64 a predetermined distance. Thus, the pair of aligned spaced apart roller means 62 form a narrowing point or bottleneck region 69 having a spacing somewhat less than the dimension of cavity 64.

Cut-off punch cuts the staple wire to correct length and forms staple points.

Punch block 57 holds slidably holds punch 56 and helps to align parts 58, 59 and 60.

Cut-off die 58 acts as a die for punch 56 and also is used as a bushing for roller and to guide wire.

Stripper block 59 guides punch 56 and acts as a bushing for the roller 62.

The forming die 60 guides wire and helps start the forming of the staple.

Pusher punch 70 generally has an upper knob section 71, an elongate body section 72 and a forming head section 73. Upper knob section 71 is configured for being clamped into the drive member 43 of a conventional type staple forming device 17 of machine 10. The length of body section 72 may be selected, for example, empirically, to suit the particular application or type of staple forming device 17 being utilized. Of particular importance with regard to the present invention is the design and configuration of the staple forming head section 73 of pusher punch 70. The tip has a transverse concave groove or channel 75 dimensioned for receiving a portion 91 of the wire 23 to form the new and improved staple 90 base section 91. Channel 75 provides a guide means for holding the staple in place, via guide walls 76, during the staple forming process. The radius of curvature (0.007″) of channel 75 is selected to accommodate a portion 91 of wire strip 44 diameter to help guide and hold the wire base section 91 in place while the pusher punch 70 is driven downwardly into die cavity 64. At each end of channel 75 a channel curvature or contoured corner 77 is provided having a predetermined radius of curvature. The exact or preferred radius of curvature, for example 0.006", may be calculated or determined empirically, with consideration to the type of metal/alloy and diameter of wire 44, to substantially, if not entirely, eliminate any cracks 48 from being produced. Thus, a new type staple 90 may be formed whereby the legs 92, 93 are bent, not at a sharp (virtual ninety degree) angle 46, but at a gradual radius of curvature 77 selected to eliminate or substantially reduce the stresses at the point of bending.

Another feature of the new pusher punch 70 design which may be combined with contoured corners 77, are inwardly sloped walls 78 having a predetermined relief angle 79 or slope. This relief angle 79 allows for over bending of the staple wire 44 (see FIG. 6). The inwardly sloped walls 78 enable the staple leg ends to bend or tilt slightly inward as the aligned roller means 62 squeezes or presses the staple legs 92, 93 about the contoured corners 77. Accordingly, it has been discovered that by enabling this over bending to occur, the inherent spring back effect which resulted in the prior art non-parallelism of the prior art staple legs 47 as depicted in FIG. 3 may be substantially controlled or utilized such that new and improved staple legs 92, 93 are substantially more normal relative to base portion 91, and with relative parallelism (see FIG. 7) as compared to the prior art staples 45 (see FIG. 3). Thus in accordance with the present invention, the staple legs 92, 93 are slightly over-bent inwardly and when released from the clamping effect of rollers 62, they spring back to form staple 90.

Figure 9B:
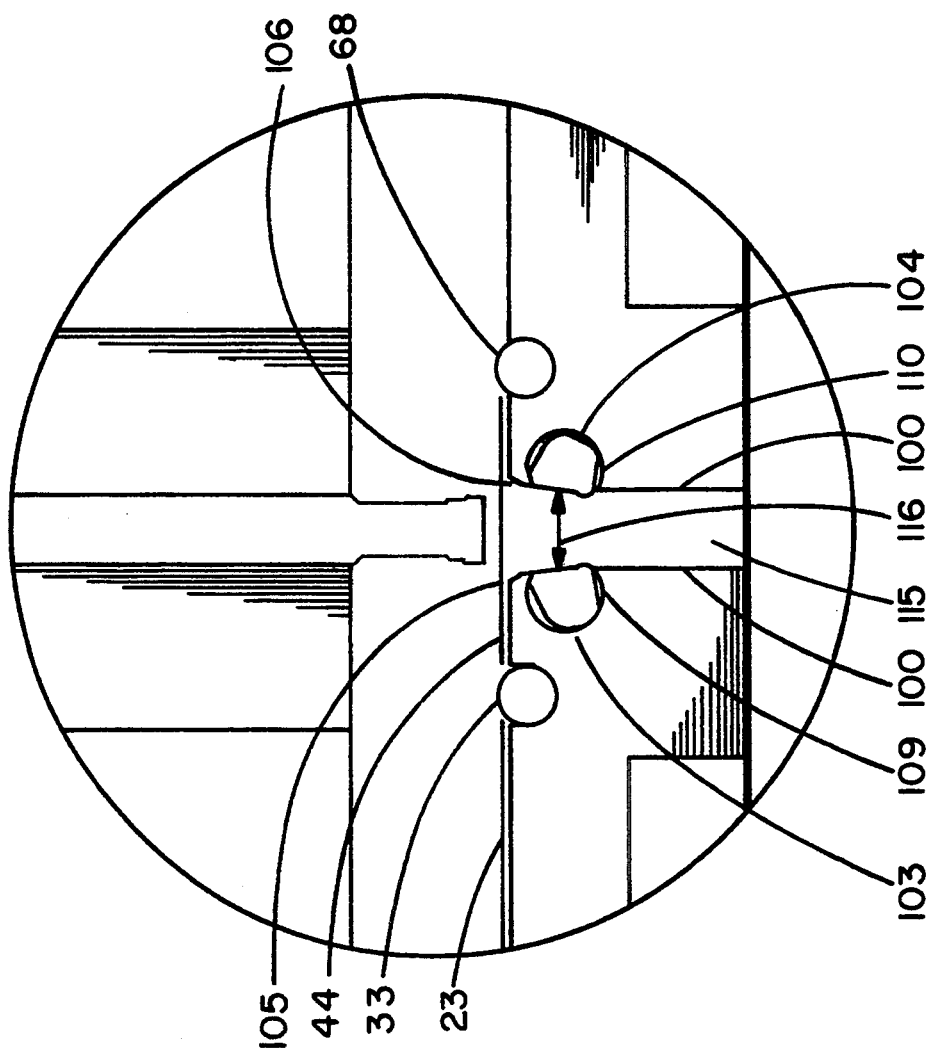
FIG. 9 is a plan view of a rocker die alternative embodiment of the present invention.
Figure 9A:
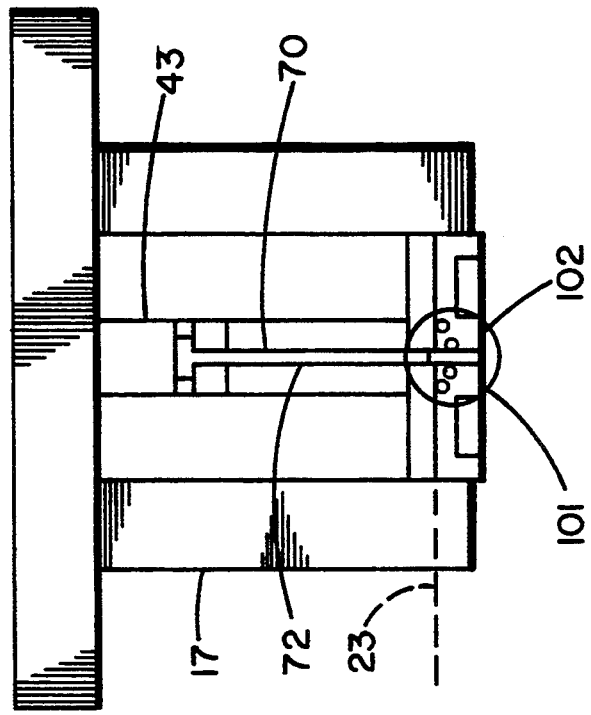
Figure 10A:
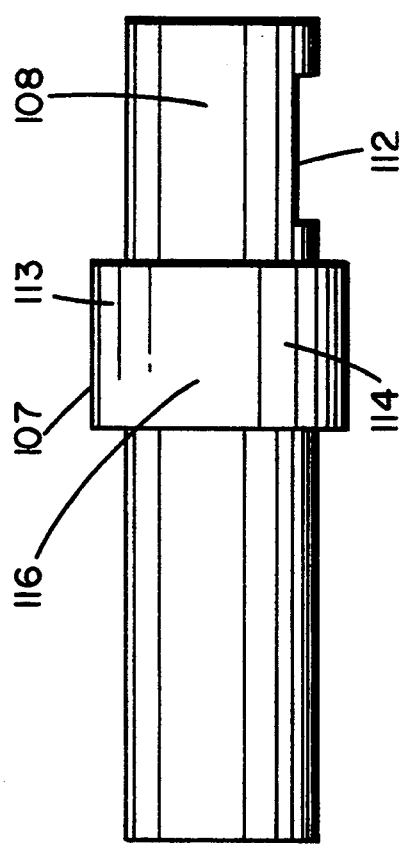
FIG. 10A, 10B and 10C are illustrative views of the rocker members illustrated in FIG. 9.
Figure 10C:
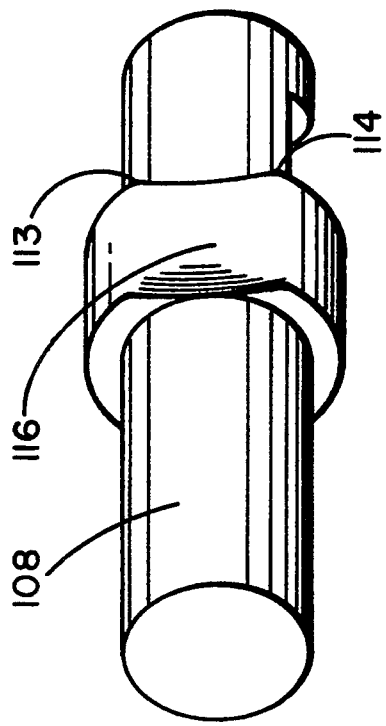
Figure 10B:
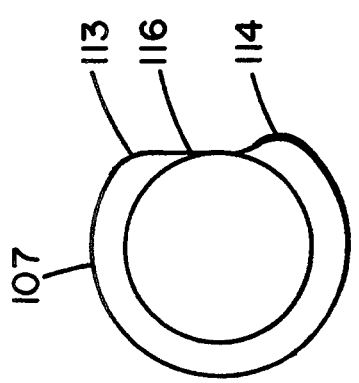
Figures 11A, 11B:
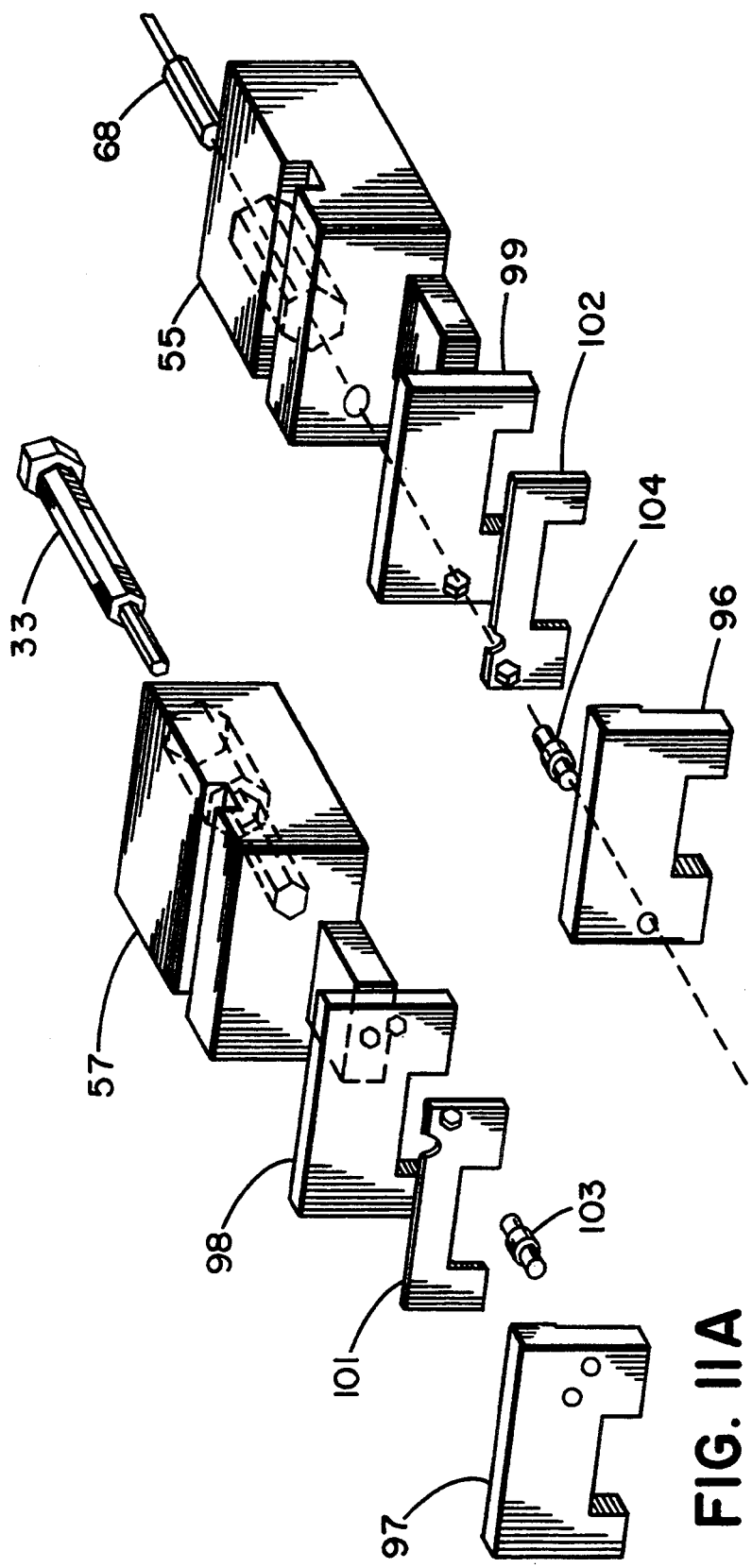
FIG. 11 is an exploded view of the rocker die assembly shown in FIG. 9.

With reference to FIGS. 9, an alternative embodiment of the invention is illustrated. As noted above, some of the important objects of the invention are to produce a staple 90 having contoured bends 77 and parallel staple legs 92, 93 which are substantially perpendicular to base portion 91. Previously stated, the preferred embodiment uses a set of rollers 62 to virtually eliminate unwanted slivers being created due to prior art scrapping of the cut staple wire 39 against the walls of the forming dies 32.

In accordance with the alternative embodiment of the present invention, the walls of forming die sections 101, 102 are spaced apart sufficiently so as not to scrapping engage legs 92, 93 of the staple 90 being formed in accordance with the present invention.

A pair of aligned rocker die members 103, 104 are rocking or pivotally mounted each to a respective forming die 101, 102. Each rocker die member 103, 104 is located substantially at the top or upper corner 105, 106 of each respective die section 101, 102 to virtually define the upper corners thereof.

Each rocker die member 103, 104 comprises a somewhat lima bean shaped cam 107 affixed to or integrally formed with a generally rod shaped pivot member 108. Each rocker die member 103, 104 is pivotally mounted within an alcove 109, 110, provided in die sections 101, 102, respectively. Since conventional mounting techniques may be used for rocking or pivotally mounting the rocking die members 103, 104, detail description thereof will not be provided to avoid prolixity. Briefly stated, however, the rod 108 projects outwardly on both sides of cam member 107, with each end being inserted into and rotatably mounted within a respective aligned hole or alcove 111, 112. Each respective cam member 107 being partially received within alcove 109, and having portions of their heel sections 113, and nose sections 114 extending beyond the respective die walls 100 and into die cavity 115. Concave section 116 of cam members 107 is contoured with a curvature similar to but somewhat greater than the radius of curvature 77 of the forming punch 70. Rod 108 may be spring biased in conventional manner or dimensional to have a weight distribution such that a rotational torque is effected causing the nose portion 114 of each cam 103, 104 to project outwardly into die cavity 115 The extent of this projection is selected such that each nose portion 114 contacted by the forming punch 7, i.e., generally by the punch head 73 with the downward motion of the forming punch 7 into die cavity 115.

The cut-off punch 33 cuts wire to length 44 and forms sharp points on the end of the staple legs.

The punch block 57 holds cut-off punch 33, stripper block 98, forming die 101, cutoff die 97 and helps keep them in alignment.

The stripper block 98 align punch 33 with die 97, and acts as a bushing for rocker die 103, while also holding ball plunger which orientates the rocker die.

The forming die 101 helps guide wire and starts the formation of the staple legs.

The rocker dies 103 and 104 form the staple legs about the forming punch.

The cut-off die acts with punch to cut wire,and acts as a bushing for rocker die 103,and helps to guide wire.

The ball plunger orientates the rocker die.

Probe 68 senses that wire has fed through the tooling.

The probe block 55 helps align and hold parts 99, 102 and 96.

Probe sending block 99 holds probe and ball plunger, and acts as a bushing for rocker die 104.

Forming die 102 helps guide wire and starts the formation of the staple legs.

Probe receiving block 96 acts as a bushing for rocker die 104 and helps guide wire.

The abutting of the pusher forming punch 70 against each of the nose 114 sections of the rocker die members 103, 104 causes a rotation of each rocker die member 103, 104 about the longitudinal axis of its respective rod member 108. This rotational motion being imparted to each cam member 107 causes the respective heel portions 113 to inwardly squeeze the staple wire 44 about the curvature 77 of punch head 70, with the nose 114 sections being urged outwardly each toward its respective alcove 109, 110.

As noted above, the concave section 116 of each cam member 107 is dimensional to accommodate the radius 77 of the forming punch 70 head 73, with the nose 114 section being pushed outwardly by said punch head 73. In other words, the concave section 116 enables the cam member 107 to virtually wraparound the curvature 77 of the head 73 with the downward motion of the pusher forming punch 70. In this manner, the staple wire blank 44 is bent to form the desired staple 90.

With reference now to FIGS. 12 and 13, another alternative embodiment of the invention is shown as a spring loaded forming die. The spring loaded forming die is designed to relieve pressure on the wire as it is formed. It can be used alone or in combination with rollers 62 or rocker forming dies 103 and 104. The spring loaded dies are designed to deflect a small amount, e.g. 0.003–0.005 inch, away from the nose 77 of the forming punch 70 as the punch nose 77 passes by, thereby relatively stopping the pressure on the wire and avoiding the cracks, slivers and thinning of wire.

In style 1 the relief angle after the bend radius of the forming dies 118 and 119 closely matches the inwardly sloping walls 78 of punch 70 allowing the spring loaded forming dies 118 and 119, or 120 and 121 to bend the wire 44 around the punch relief angle 79 without damaging the wire.

The forming dies are allowed to slide because of a small amount of clearance with the surrounding parts. The forming dies are held in the closed or tight position by springs 122.

A small amount of material is removed from the locating slot at this point A to allow the forming die to slide back away from the nose 73 of the forming punch. Material is removed at location B of the forming die to make room for the flat spring. Spring pressure at this point pushes the forming die towards the forming punch.

The punch block 123 performs the same functions as above described with the added function of holding the flat spring 122 which screws to its side.

The probe block 124 provides the functions above noted, with the added function of holding the flat spring 122 which is screwed to its side.

Stripper block 125, probe sending block 126, probe receiving block 127 and cut-off die 128 perform similar functions as above but have clearance so that spring 122 can push on the forming dies without touching them.

Forming dies 118, 119, 120 and 121, function as previously noted with the addition that they can move away from the forming punch to eliminate the pressure on the bend radius of the staple leg 46. This prevents the wire from stretching, thinning and cracking. This movement is accomplished by giving extra clearance between the forming dies and the punch block 123 or probe block 124. The spring preloads the forming dies so they push towards the forming punch.

The term "medical staple" shall hereinafter mean a metal type staple 90 having a pair of relatively parallel legs 92, 93, having bend portions 97 connecting said legs to a base member 91 of the staple and being usable on animal and human tissue such as, for example, to close a wound by stapling in contrast with a fiber suture to sew the parts together.

The term "relief angle" shall hereinafter mean an angle to enable selective over bending of a piece of metal or wire beyond a point or location such that upon release of the wire a portion of the metal/wire springs or bounces back substantially to a desired or predetermined disposition relative to other portions of the metal/wire.

While certain specific embodiments have been set forth the invention for the sake of illustration to persons skilled in the art, it is not intended to be limitative. For example, although the specific embodiments contemplate a roller or rotative cam to substantially eliminate scraping of the wire against the die members, other formats can be utilized.

I claim:

1. A forming punch having particular utility to facilitate the forming of a new and improved medical staple having a pair of spaced apart projecting leg portions (92, 93) each with a relatively gradual bend portion (97) defining a desired radius of bend curvature (77) with a base member (91), comprising:
   a body portion (72); and
   a head member (73) integrally formed with said body portion, and having tapered wall portions (78) defining a relief angle (79) of taper, and a tip portion (74) with a pair of transverse side wall members (76) and an upper transverse channel wall member (80) defining a transverse staple wire receiving groove (75), said upper transverse channel wall member (80) having upwardly curved end portions (77) each defining a predetermined radius of bend curvature substantially similar to the desired bend curvature of the medical staple bend portions (97).

2. A forming punch as in claim 1, wherein:
   the body portion (72) comprises an elongate flat rectangular shaped metal rod.

3. A forming punch as in claim 1, wherein:
   the staple wire receiving groove (75) being dimensioned for snugly receiving and holding a preselected staple wire (44) dimension.

4. A forming punch as in claim 1, wherein:
   the relief angle (79) of taper being predetermined relative to the dimension and type of the medical staple being formed.

5. A forming punch as in claim 1, wherein:
   the radius of bend curvature (77) is predetermined to define and control the bend portion (97) curvature of the medical staple (90) to substantially reduce cracking and thinning of the medical staple at the bend portion (97).

6. A forming punch and die, in combination comprising:
   a pusher type forming punch (70) having an elongate body portion (72) and a head member (73), said head member having a tip portion with a pair of spaced apart side wall members (76) and an upper wall member (80) defining a contoured staple wire receiving groove (75), said upper wall member having curved end portions (77) each defining a selected radius of bend curvature; and
   a forming die (60) having a pair of spaced apart rail members defining a die cavity (64) and a pair of movable glide members (62, 103, 104), said die cavity being dimensioned for receiving therein portion of said forming punch.

7. A forming punch and die as in claim 6, wherein:
   the forming punch has a generally elongate flat rectangular configuration with said wire receiving groove being concave and extending transversely across said tip portion and having a predetermined radius of curvature.

8. A forming punch and die as in claim 6, wherein:
   the head member has inwardly sloped wall portions (78) defining a relief angle (79).

9. A forming punch and die as in claim 6, wherein:
   the glide members each comprise a roller (62) rotatably mounted to a respective rail member.

10. A forming punch and die as in claim 6, wherein:
    the glide members each comprise a cam (107) having a concave section (116) and a nose section (114) and a hell section (113), rockingly mounted to a respective rail member.

11. A forming punch and die for forming a metal wire strip (44) into a medical staple (90) to have relatively parallel staple legs (92, 93) substantially without metal wire cracks (48) along a relatively gradual wire bend curvature (97), in combination comprising:
    a pusher forming punch having a body portion (72) and a head member (73), said head member having tapered side wall portions (78) defining a predetermined relief angle (79) of taper, and having a contoured tip portion with a pair of spaced apart transverse and downwardly projecting wire retaining wall members (76) and an upper transverse curved ceiling wall member (80) defining a transverse staple wire receiving groove (75), said ceiling wall member having upwardly curved end portions (77) each having a curvature for constraining the metal wire strip about the wire bend curvature (77) to substantially reduce any cracking and thinning of the metal wire strip while forming the medical staple (90); and a forming die (60) having a pair of spaced apart rail members each having an upper bevelled edge corner (61), and a pair of aligned roller means (62) each rotatively mounted to a respective rail member and projecting outwardly beyond the respective die walls (63) which define a die cavity (64), said aligned roller means being spaced apart a distance to enable disposition of portions of said pusher forming punch, whereby with the metal wire strip (44) being positioned longitudinally within said wire receiving groove (75) and with said pusher forming punch being urged between said roller means (62), the outwardly extending metal wire strip on both sides of said head member are bent over the respective curved end portions (72) of said pusher head member for effecting the gradual wire bend curvature (97) of the staple legs (92, 93).

12. A forming die assembly having particular utility for forming a metal wire strip (44) into a medical staple (90) to have relatively parallel staple legs (92,93) substantially and relatively without metal wire cracks (48) along a relatively gradual wire bend curvature (97), comprising:

a punch block (123) having a projecting mounting beam (130), a a stripper block configured for being mounted on said mounting beam (130), a first forming die member (118) slidably mounted unto said mounting beam (130) in slidable juxtaposition between said stripper block and a cut-off die (128);

a probe block (124) having a projecting mounting beam (131) and being spaced from and aligned with said punch block to define a die cavity, a probe sending block (126) configured for being mounted on said mounting beam (131), a second forming die member (119) slidably mounted unto said mounting beam (131) in slidable juxtaposition between said probe sending block (126) and a probe receiving block (127) in spaced alignment with said first forming die member;

a first spring means (122) for biasing said first forming die member (118) inwardly into said die cavity;

a second spring means (122A) for biasing said second forming die member (119) inwardly into said die cavity toward and in alignment with said first forming die member.

13. A forming die assembly as in claim 12, including:

a pusher forming punch (70) having tapered side walls (78) and a contoured tip portion (73).

* * * * *